(12) United States Patent
De Jong et al.

(10) Patent No.: US 6,322,512 B1
(45) Date of Patent: *Nov. 27, 2001

(54) ULTRASOUND CONTRAST IMAGING

(75) Inventors: Nico De Jong, Krimpen aan den Ijssel; Peter Frinking, Rotterdam, both of (NL)

(73) Assignee: Acuson Corporation, Mountain View, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/341,857
(22) PCT Filed: Jan. 19, 1998
(86) PCT No.: PCT/GB98/00159
§ 371 Date: Sep. 7, 1999
§ 102(e) Date: Sep. 7, 1999
(87) PCT Pub. No.: WO98/32378
PCT Pub. Date: Jul. 30, 1998

(30) Foreign Application Priority Data
Jan. 22, 1997 (GB) .................................... 9701274

(51) Int. Cl.[7] ............................................. A61B 8/00
(52) U.S. Cl. ............................................. 600/458; 600/438
(58) Field of Search ................................... 600/458, 438, 600/485, 486, 323–334, 2, 3, 437

(56) References Cited

U.S. PATENT DOCUMENTS

| 5,195,520 | 3/1993 | Schlief et al. . |
| 5,255,683 | * 10/1993 | Monaghan ............................ 600/443 |
| 5,456,257 | 10/1995 | Johnson et al. . |
| 5,560,364 | 10/1996 | Porter . |
| 5,685,310 | * 11/1997 | Porter .................................. 600/458 |
| 5,694,937 | * 12/1997 | Kamiyama ............................ 600/446 |
| 5,735,281 | 4/1998 | Rafter et al. . |
| 5,833,613 | 11/1998 | Averkiou et al. . |
| 5,957,845 | * 9/1999 | Holley et al. ......................... 600/440 |

FOREIGN PATENT DOCUMENTS

| 0 398 935 B1 | 2/1989 | (EP) . |
| 0 586 875 | 2/1989 | (EP) . |
| 0 644 776 B1 | 4/1993 | (EP) . |
| 0 717 617 B1 | 8/1994 | (EP) . |

* cited by examiner

Primary Examiner—Marvin M. Lateef
Assistant Examiner—Maulin Patel
(74) Attorney, Agent, or Firm—Craig A. Summerfield; Brinks Hofer Gilson & Lione (57) ABSTRACT

The invention provides a non-invasive method and apparatus for improved ultrasonic imaging and for measurement of ambient pressure, temperature or gas concentration using non-invasive ultrasound contrast imaging techniques.

15 Claims, 9 Drawing Sheets

Fig. 7 ns relates to ultrasound contrast imaging methods and apparatus and more particularly to # ULTRASOUND CONTRAST IMAGING This application claims the benefit of foreign priority pursuant to 35 U.S.C. §§119 and 371 to PCT/GB98/00159, filed Jan. 19, 1998 and corresponding application in Great Britain, 9701274.4, filed Jan. 22. 1997, the disclosure of which are incorporated herein by reference.

The present invention relates to ultrasound contrast imaging methods and apparatus and more particularly to measurement of pressure and/or temperature in a body.

In particular the invention provides non-invasive real time determination of temperature, pressure, gas concentration etc in the blood. This is extremely difficult to achieve in, for example, internal organs and, for example, real time determination of temperature of an internal organ during treatment can provide the physician with valuable information allowing enhanced treatment.

This enables local determination of organ perfusion and local determination of ambient pressure, temperature or gas concentration.

The inventive technique is substantially better than alternative techniques to achieve the same objective since organ perfusion measurements require x-ray technology and ambient pressure and gas content measurements respectively require a pressure catheter and a blood sample.

U.S. Pat. No. 5,456,257 discloses an ultrasonic diagnostic system which detects the presence of coated microbubble contrast agents in the body of a patient by transmitting ultrasonic energy which causes the destruction of the coated microbubbles and detects the microbubble destruction through phase insensitive detection and differentiation of echoes received from two consecutive ultrasonic transmissions.

According to the present invention there is provided an ultrasound contrast imaging method comprising generating a first, relatively high power, acoustic field for a first predetermined number of cycles, and following a predetermined time delay generating a second relatively lower power acoustic field for a second predetermined number of cycles, said first predetermined acoustic field causing, in use, power enhanced scattering and said second predetermined acoustic field being below the threshold for power enhanced scattering and causing scattering providing information about possible generated free gas bubbles.

Power enhanced scattering is defined as providing an acoustic pulse at an amplitude at least sufficient to cause a change in the acoustic properties of the region of interest to, for example, cause bubbles to be released from the microcapsules.

Preferably the acoustic field has a frequency of 100 kHz to 10 MHz.

The present invention also provides apparatus for ultrasound contrast imaging comprising means for generating a first relatively high power acoustic field for a first predetermined time period, timing means for generating a predetermined delay time, and means for generating a second relatively low power acoustic field for a second predetermined period following said predetermined delay time.

Preferably the apparatus comprises receiver means for receiving a signal in a period following the generation of the second relatively low power acoustic field.

Preferably the means for generating a second relatively low power acoustic field comprises further timing delay means for repeating said low power acoustic field after a further predetermined delay. Preferably the apparatus includes signal receiver means for interrogating a received signal during said further predetermined delay.

In a preferred embodiment the apparatus comprises time sequencing means for repetitively supplying a series of relatively low power acoustic fields with a predetermined time delay interposed between each relatively low power acoustic field and including receiver means for receiving and interrogating a received signal during each predetermined time delay.

Preferably the apparatus includes means for determining from the received signal whether any generated small bubbles are still present and means for terminating said sequence of relatively low acoustic power signals on determination that no small bubbles are present.

The apparatus also preferably includes means for selectively adjusting the insonifying frequency of the acoustic field to adjust the disappearance period of the generated free gas bubbles.

Embodiments of the present invention will now be described, by way of example with reference to the accompanying drawings in which.

INTRODUCTION

The present invention provides an apparatus and a method of measuring either pressure, temperature or gas concentration by a non-invasive technique.

The measurement of instantaneous pressure or temperature in, for example, an internal organ of an animal is extremely difficult by non-invasive techniques.

The present invention provides such an apparatus and method.

The general principle will be explained followed by specific examples. The animal is injected or otherwise supplied with a suspension of microcapsules suspended in a suitable liquid, for example isotonic sterile saline, such as Isoton.

Suitable microcapsules include those disclosed as "Quantison" microcapsules by Andaris Limited, and described in WO92/18164 (U.S. Pat. No. 5,518,709), WO94/08627 and WO96/15814 (U.S. Ser. No. 08/676,344 filed Jul. 19 1996), all of which are incorporated herein by reference. The microcapsules are made by spray-drying a solution of serum albumin to form hollow microcapsules generally of diameter 1 to 10 μm; for example 90% may have a diameter of 1.0 to 9.0 μm or 1.0 to 6.0 μum, as measured in a Coulter Counter Multisizer II. However, any gas containing microcapsule, microsphere or microparticle which releases the gas on irradiation with a non-physiologically harmful dose of ultrasound may be used in the methods of the invention.

These microcapsules are full of air or other suitable gas and for the purposes of the present invention it will be assumed that they are full of air. The animal, for example a human, is preferably injected in a blood vessel such as a vein or an artery, depending on the region which is to be studied. Organs to be studied include the heart, kidneys and liver.

The general principle of the present invention is that these microcapsules are subjected to an acoustic field of high power. This field causes the air within the microcapsules to be expelled thereby releasing small free air bubbles.

These free small air bubbles are absorbed into the liquid at different rates dependent on the pressure and also dependent on the temperature. If the pressure within a vessel is known or is constant then the temperature can be measured.

If the microcapsules are filled with another gas then this will result in a different signal and a different persistence resulting in more information of the ambient (blood) parameters.

Thus for example if an internal organ is subjected to an increase in temperature for therapy application it is fairly important to know the temperature and this can be measured using this technique if it is assumed that the pressure remains constant.

Similarly for other vessels the temperature can be assumed to be constant and therefore the pressure can be measured.

The small free air bubbles reflect or scatter a very sensitive signal which is readily detected. Therefore their rate of disappearance into the surrounding liquid is readily detectable and since the time taken for total (say for example 90%) dissolution is dependent on pressure and temperature this can be accurately measured.

Referring to the drawings, the apparatus comprises a transducer. Three different types of transducer are possible for contrast imaging and these may be provided as follows:

a1 A transducer using the fundamental resonance frequency and using the harmonics, especially the third harmonic.

a2 A transducer with two frequency peaks, e.g. one peak at 1 MHz and the other at 2 MHz. The peaks themselves are relatively small banded (20–30%), the sensitivity between the two peaks is relatively low (preferably below –10 dB below the peak sensitivities at 1 MHz). The sensitivity at 1 and 2 MHz are more or less the same. Other combinations can be provided too, for example 1.5 and 3 MHz, 2.5 and 5 MHz etc. Such a transducer can be provided, for example, by adapting the ¼ λ layer especially by choosing the right impedance.

Figure 1:
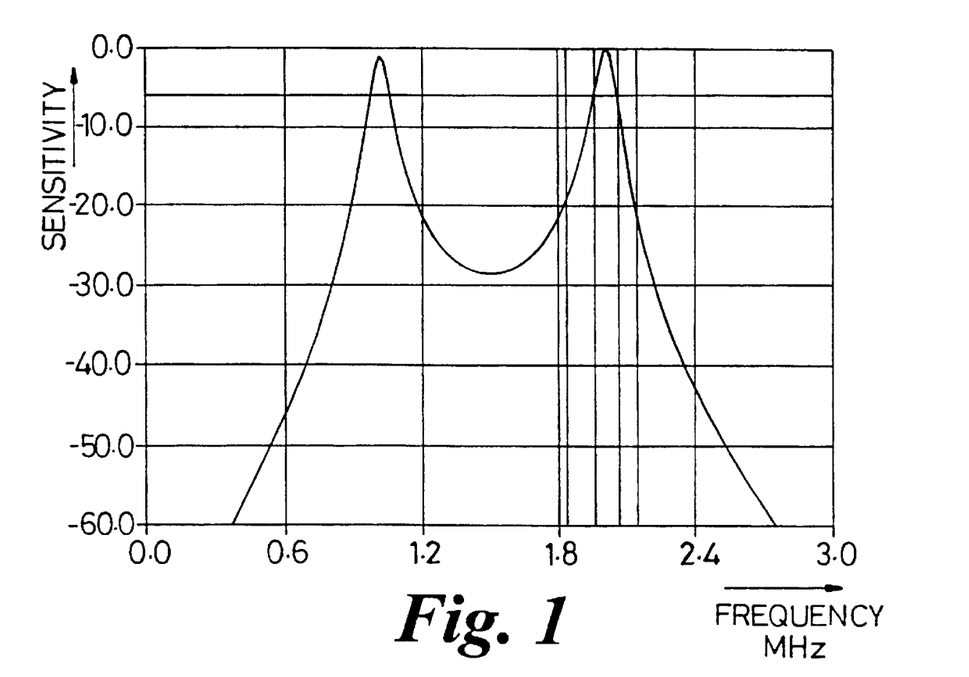
FIG. 1 shows a frequency characteristic waveform of a first transducer with two distinct peaks used in the present invention.

An example of such a design is given in FIG. 1 the frequency response being shown with two clear peaks at 1 and 2 MHz.

a3 A transducer with a single frequency peak, e.g. a peak at, for example, 1 MHz and a broadband part at a centre frequency of, for example, 2 MHz. The first peak is relatively small banded (20–30%), and is used for a sending circuit to generate a low frequency ultrasound field with a high amplitude. The second broadband part is used for receiving the scattered signal. The main difference from transducer type a2 is that this transducer a3 is also suitable for imaging of tissue by using oily the sensitivity part around 2 MHz. Other combinations can be provided too, for example, 1.5 and 3 MHz, 2.5 and 5 MHz etc. Such a transducer can be developed, for example, by using two matching layers, the first one (close to the transducer) with a high impedance, e.g. 20 MRayls (±10 MRayls), the second one with an impedance of 3 MRayls (±2 MRayls).

Figure 2:
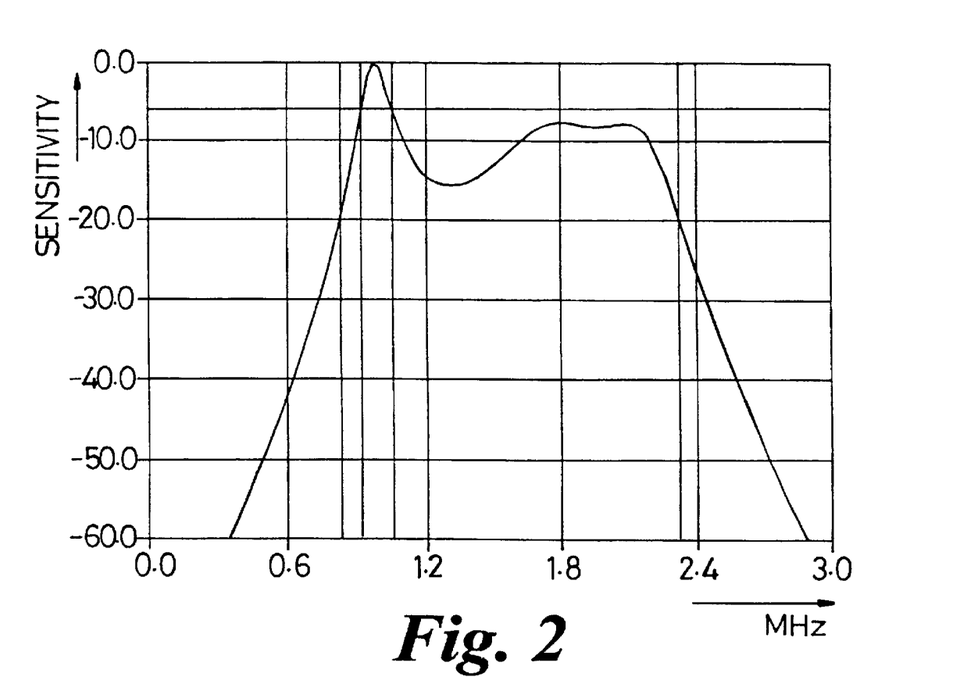
FIG. 2 shows a frequency characteristic of a second transducer with a first frequency peak and a broadband part to generate a low frequency ultrasound field with a length, amplitude and a broadband part for receiving the scattered original.
Figure 3:
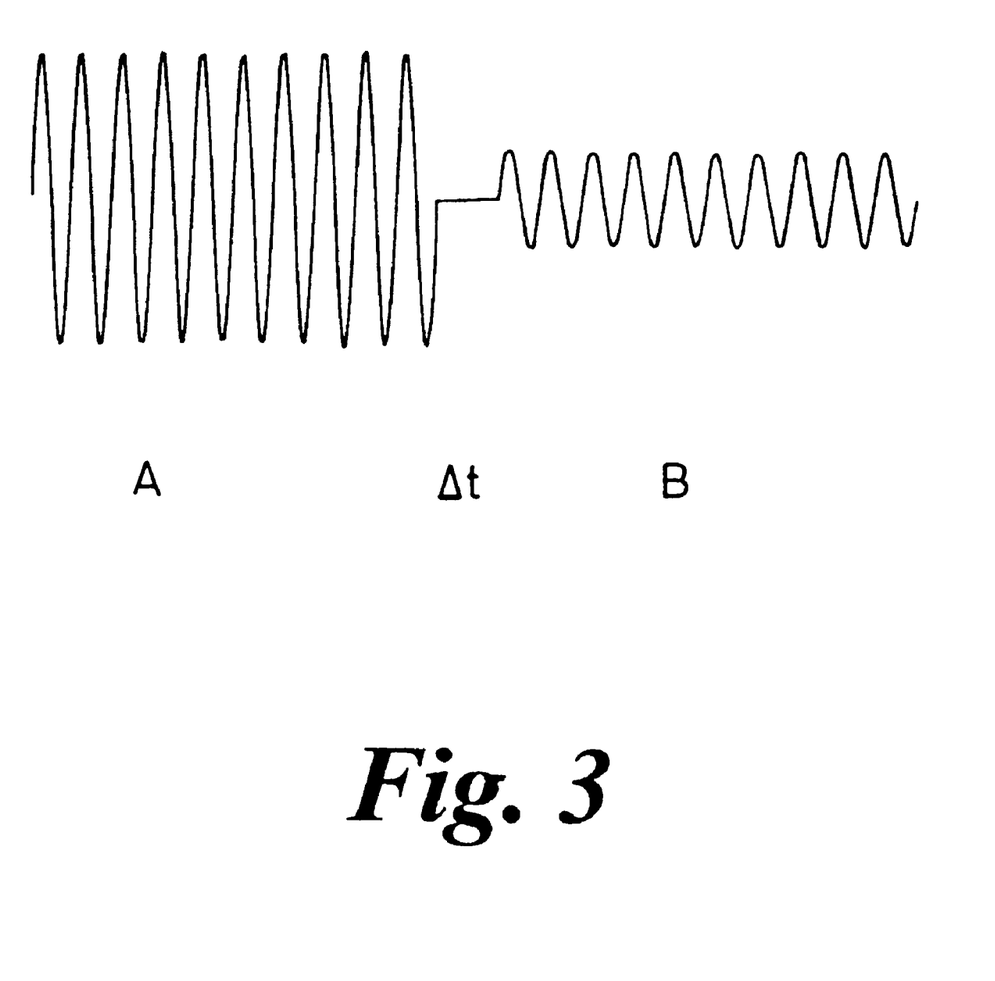
FIG. 3 shows a complex acoustic field waveform in accordance with the present invention.

An example of such a design is given in FIG. 2 the frequency response being shown with one clear peak at 1 MHz and a broadband part around 2 MHz.

b Procedure of Scanning b1 For a phased array the peak acoustic pressure amplitude decreases for increasing scanning angle. Normally this is compensated by an increasing gain of the receiving signal. For ultrasound contrast imaging using power enhanced scattering, compensation has to be carried out by increasing the transmit signal as a function of the scanning angle. The peak acoustic pressure amplitude will be then independent of the scan angle, resulting in a uniform scattering.

c Determination of Ambient Parameters (like pressure, temperature, gas concentration) is Achieved as Follows by.

c1 Generating an acoustic field as shown in FIG. 3 of a certain frequency (100 kHz–10 MHz) with an acoustic peak amplitude above the threshold for causing power enhanced scattering and a number of periods between 1 and 20, followed by a delay ($\Delta t$) and then an acoustic field with an acoustic amplitude below the threshold causing power enhanced scattering. The second complex causes scattering which gives information about the (possible) generated free gas bubbles, like the bubble sizes. This scatter information is dependent on the delay ($\Delta t$) and will decrease to zero for an increasing delay, indicating the disappearance of the free gas bubbles. Information includes the ambient temperature, pressure, gas concentration, and, by the diffusion constant, also the gas content of the free gas bubble. An example is shown in FIG. 4.

In a preferred example, the procedure is transmitting with a 1 MHz transducer and followed by transmitting and receiving with a 2 MHz broadband transducer. The transmitting consists of two sineburst; one of 1 MHz, and one of 2 MHz. In a preferred example, the first burst (A) has an amplitude of 300 V or above (equal to about 0.6 Mpascal or above) and the second burst (B) has an amplitude of for, for example ⅓ of the first pulse, e.g. 100 V for the 300 V example. The second pulse amplitude should be such as not to cause any substantial release of bubbles. The amplitude V1 and length of frequency of both bursts can be controlled. The delay between the two bursts is $\Delta t$. The used concentration is 60 μl 1.0–6.0 μm of diameter spray-dried albumin microcapsules in 1.5 l Isoton.

Although the above power figures provide the desired effect for the said microcapsules, it may be possible to achieve the power enhanced scattering with lower power values if the wall strength of the microcapsules used is lower.

The time traces of the scattering caused by burst B as function of the delay $\Delta t$ are given in FIG. 4. The figures show the received signal as measured with a 2 MHz frequency and with a delay $\Delta t$ in FIG. 4A is 1 ms, in FIG. 4B it is 10 ms and in FIG. 4C 20 ms. At t=zero the medium was insonified with a high acoustic signal of 1 MHz. As can be seen the signal has disappeared after 20 ms (FIG. 4C).

Figure 4A:
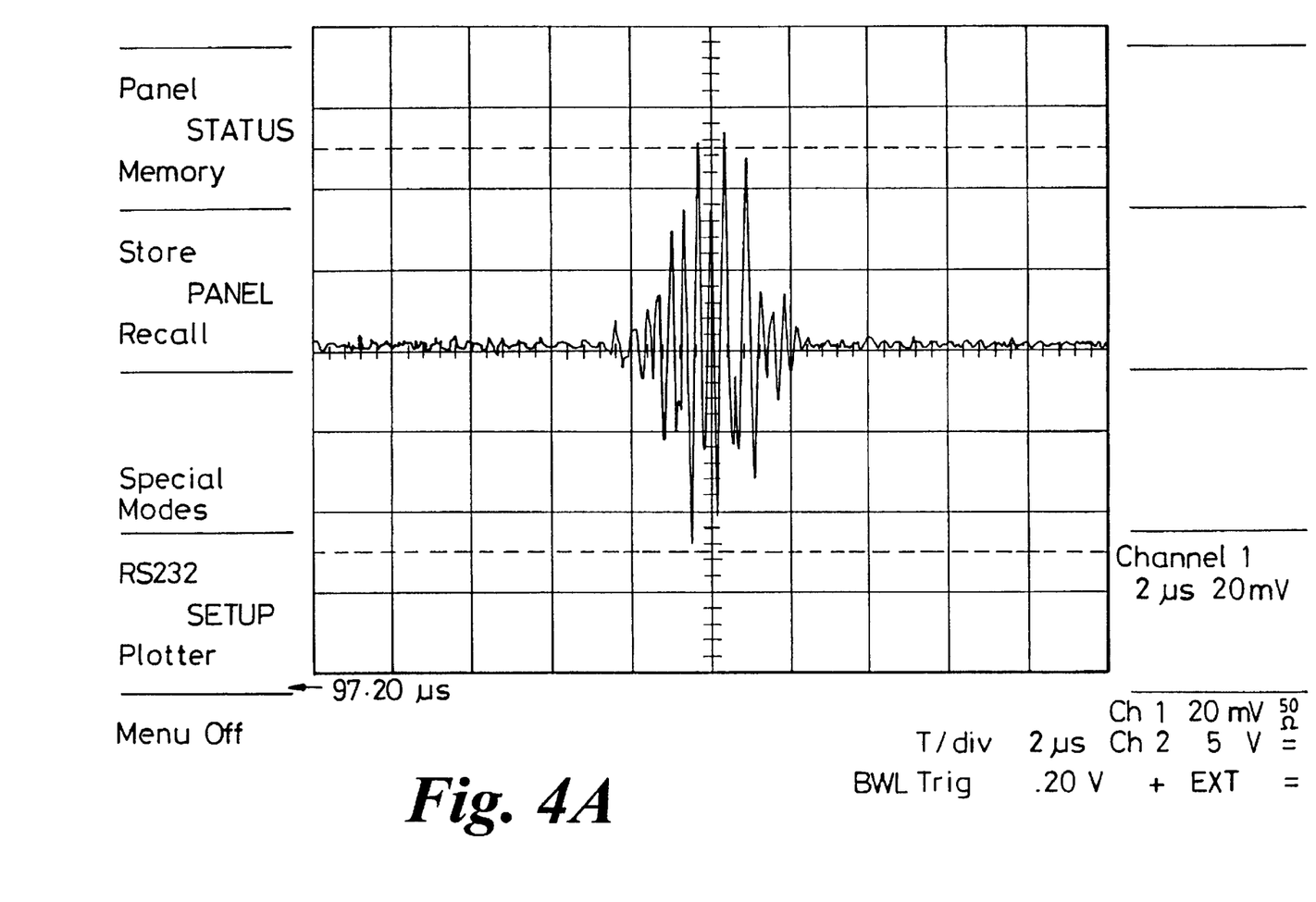
FIGS. 4A,B and C shows scatter information graphs illustrating the effects of increasing delay period At of the waveform of FIG. 3.
Figure 4B:
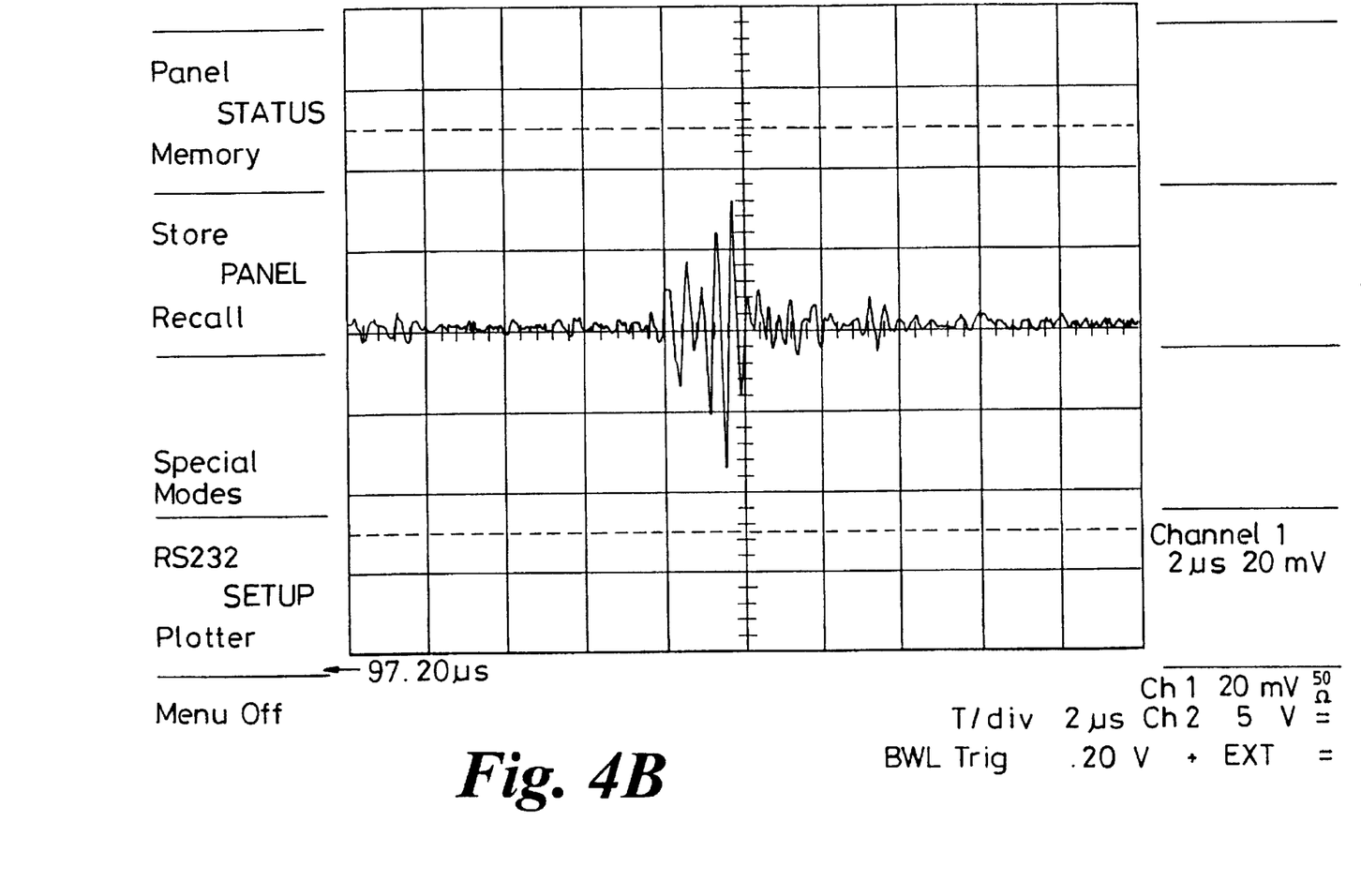
Figure 4C:
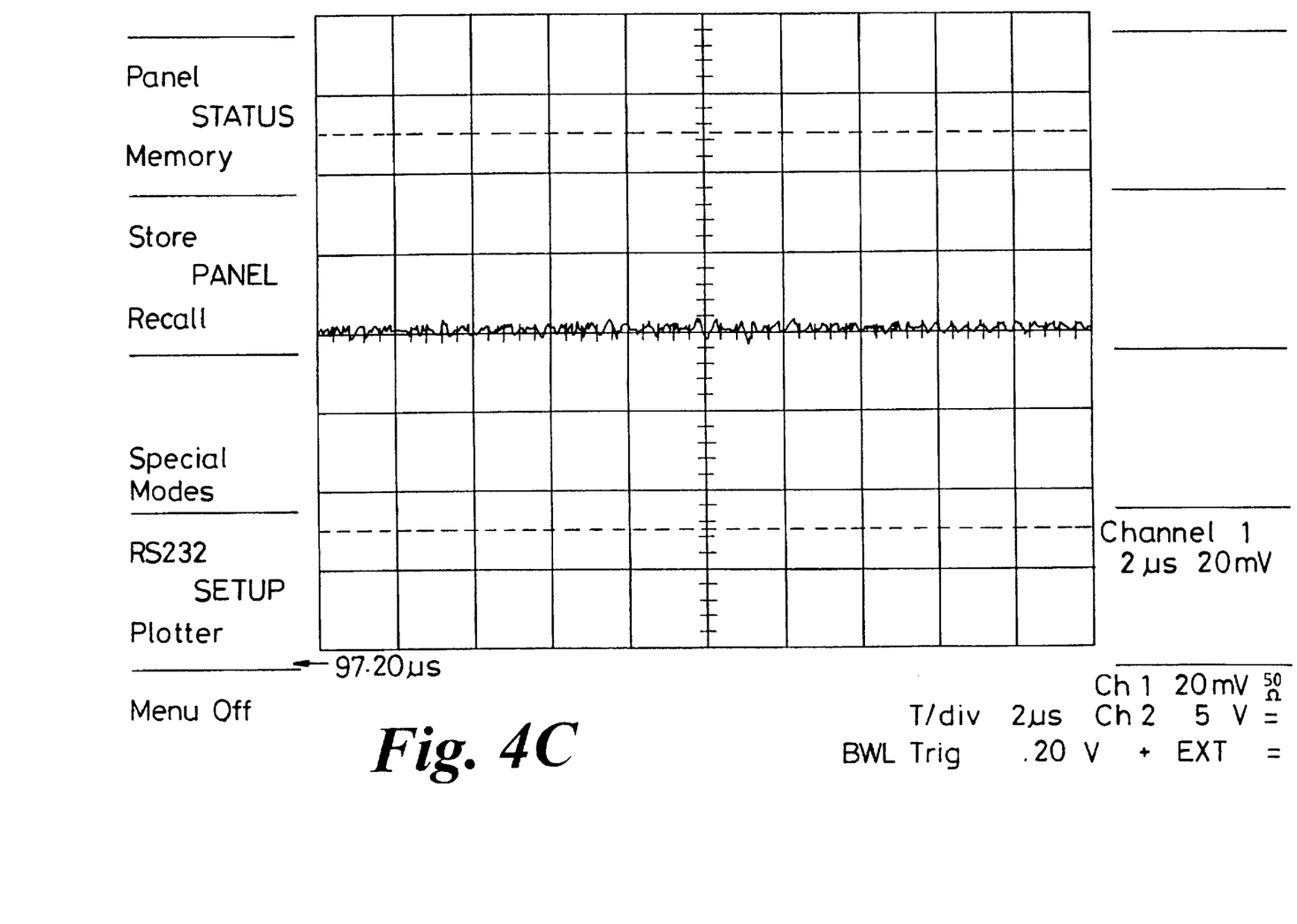
Figure 4D:
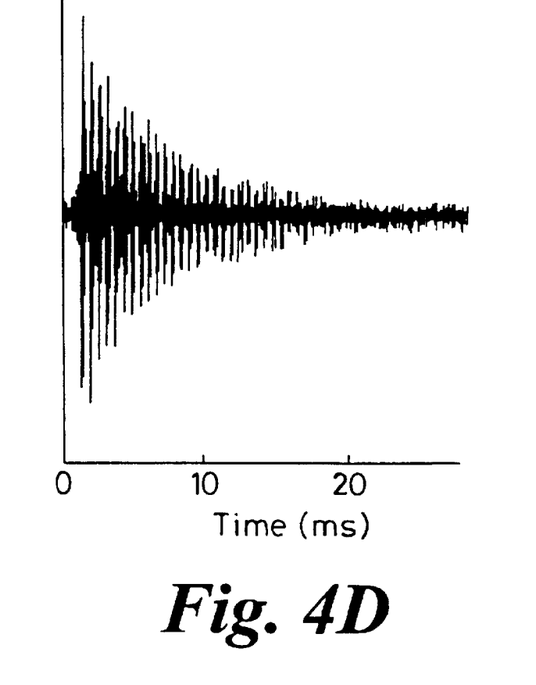
FIG. 4D illustrates the decreasing response with delay time Δt.

The signal trace is alternatively shown in FIG. 4D which shows the decrease of signal amplitude (y axis) with time (x axis).

The inventor has also found a relationship between disappearance rate and insonifying frequency. Sensing the disappearance or appearance of the released free bubble can be used for imaging.

Experimental data shows the following disappearance rates for the insonifying frequencies of 0.5, 1 and 2.5 MHz.

Figure 5:
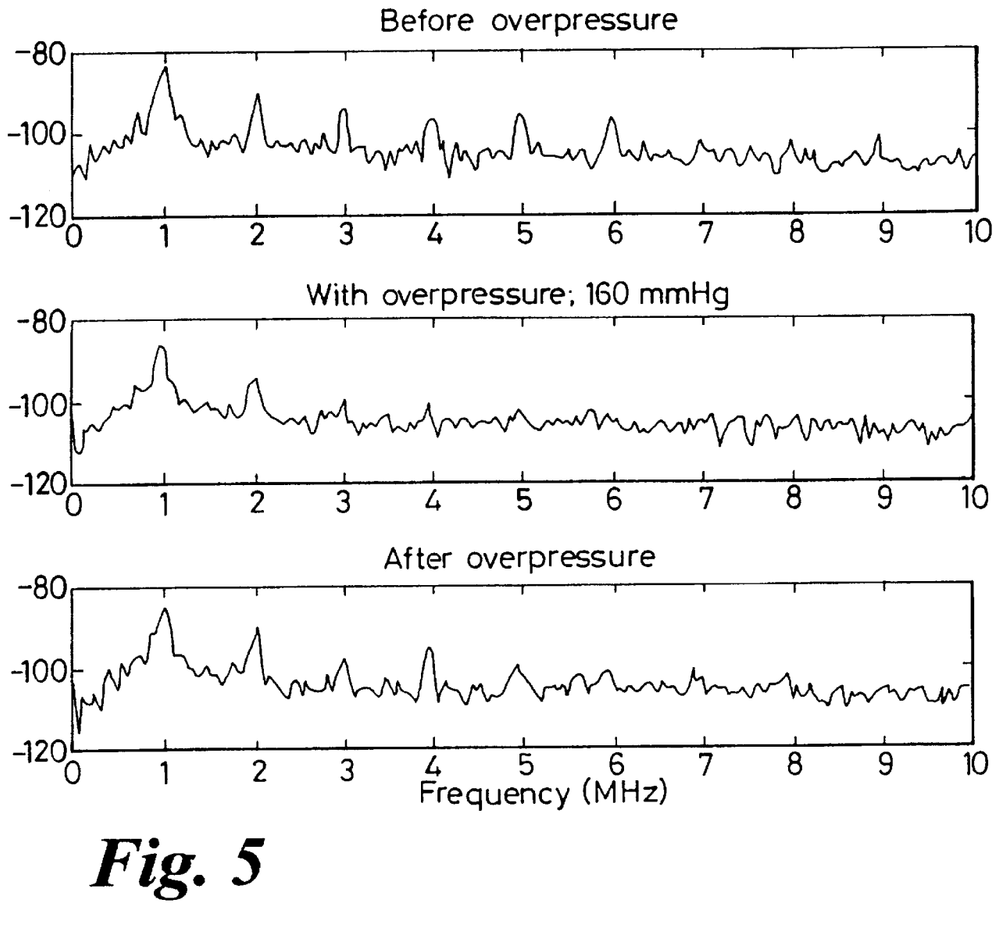
FIG. 5 illustrates a method of measuring ambient pressure with, as an example, At set to 80 μsecs.

| Insonifying freq 0.5 MHZ | Insonifying freq. 1 MHZ | Insonifying freq. 2.25 MHZ |
| --- | --- | --- |
| approx. 20 ms | approx. 10 ms | approx 2 ms | c2 An exemplary method to measure the ambient pressure is given in FIG. 5.

The delay Δt is set to 80 μs. The used concentration is 100 μl "Quantison" microcapsules in 1.5 l Isoton. Amplitude A was set to 300 V (0.51 MPascal), B to 100 V (0.17 MPascal). The insonify frequency is 1 MHz. As receiver a broadband transducer of 10 MHz is used. Measurements are made before (top panel); during (middle panel) and after (bottom panel). 160 mmHg overpressure is applied.

During overpressure, decreases of the higher harmonics were measured, together with a shift of the first harmonic, which were restored after releasing the overpressure. This provides a method for measuring the ambient pressure providing other parameters, e.g. temperature, are known or are constant.

In the fluid of interest, encapsulated air bubbles (Quantison, Andaris Ltd., Nottingham, UK) are injected with optimal concentration. A low frequency, high acoustic amplitude burst (0.5 Mhz, 1.8 MPa, 10 μs) is transmitted to excite the microspheres and to generate free air bubbles. The disappearance rate of the released air bubbles is determined by using a high frequency, low acoustic amplitude, broad band pulses (10 MHz, 25 kPa, 100% at the −20 dB level, Pulse Repetition Frequency of 1.6 kHz). Reproducible results show significant differences between persistence of bubbles as function of ambient pressures (50, 100, 150 and 200 mmHg).

Figure 8:
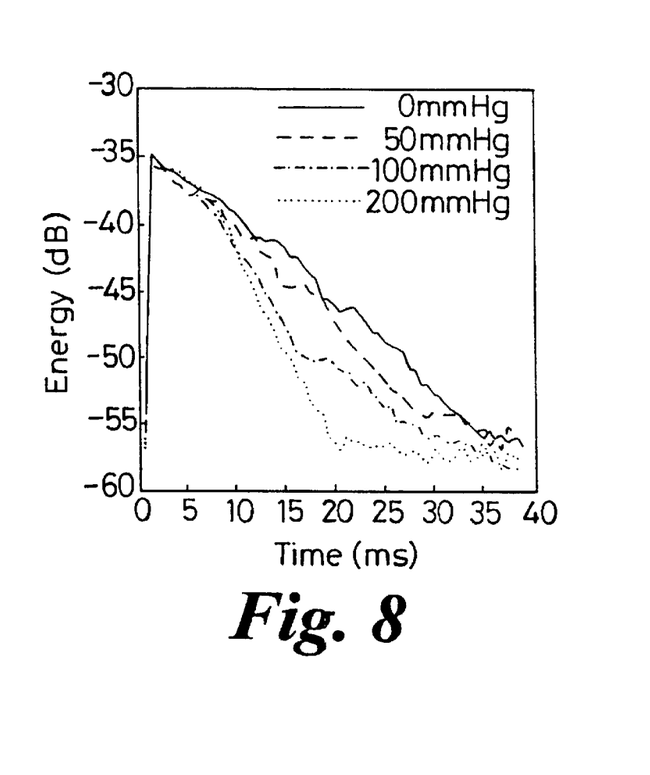
FIG. 8 shows a graph of scattered energy versus time for different surrounding pressures.

FIG. 8 shows a graph illustrating the scattered energy of released air bubbles as a function of time for four different surrounding pressures. The x axis represents time in milliseconds and the y axis energy in decibels.

The first solid line represents the scattered energy of released air bubbles at an ambient surrounding pressure. The second dotted line represents 50 mm Hg pressure, the third dash—dotted 100 mm Hg and the fourth dotted line 200 mm Hg.

A base reference energy level may be set at −55 dB.

It may be seen that the graphs for 0 (ambient) 50, 100 and 200 mm Hg cross this reference level at 33, 29, 26 and 18 millisecs., thereby enabling the pressure to be measured by extrapolation if between these levels.

The disappearance rates in Isoton and degassed Isoton were found to vary substantially. Transmitting high acoustic power with a burst of 1 MHz, transmitting and receiving (at a low acoustic power) with 10 MHz transducer the following results were achieved.

| saturated Isoton | 10–12 ms |
| --- | --- |
| degassed Isoton | 2–3 ms |

Figure 6:
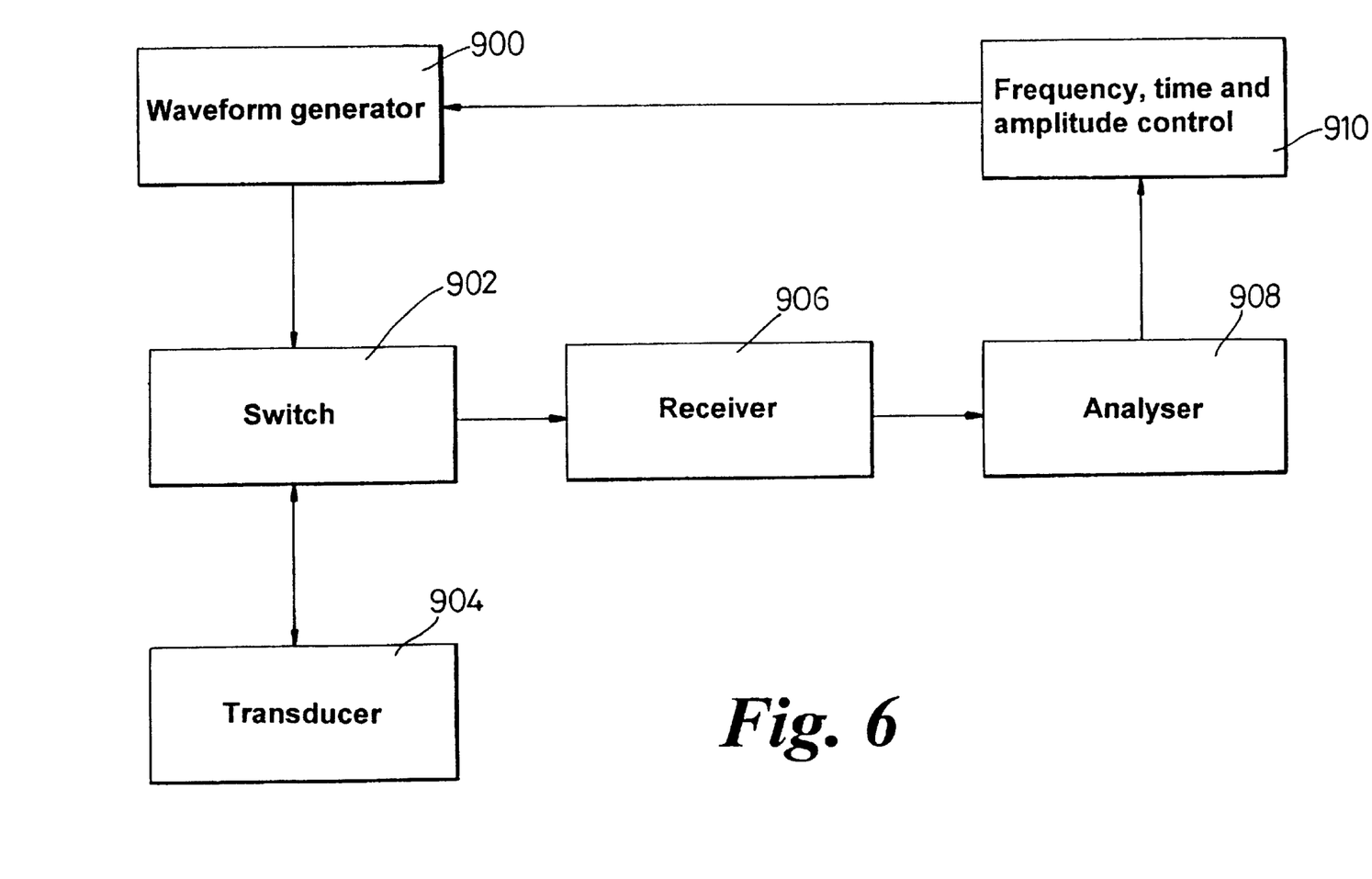
FIG. 6 shows a block diagram of an apparatus for generating and analysing the waveform of FIG. 3.

With reference now to FIG. 6, the apparatus for generating the waveform of FIG. 3 comprises a waveform generator 900 connected to a switch 902 and a transducer 904 connected to receive and transmit signals via the switch 902.

Signals from switch 902 are received by a receiver 906 the output of which is fed to a signal analyser 908. The analyser 908 is connected to a frequency time and amplitude control circuit 910 which in turn is connected to the waveform generator 900 to provide a control signal.

Figure 7:
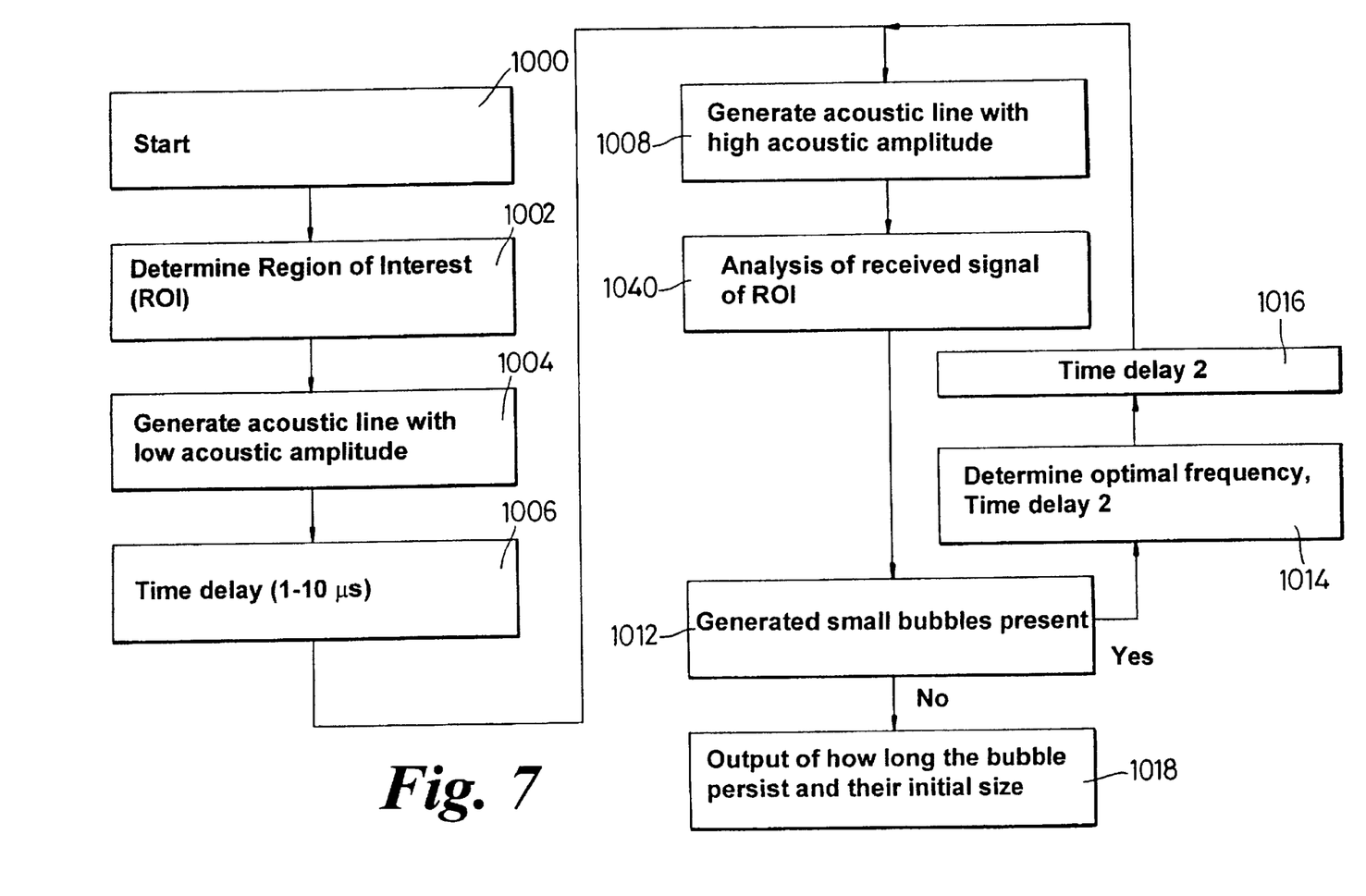
FIG. 7 comprises a flow diagram showing the sequence of events for the apparatus of FIG. 6 in generating and analysing the waveform of FIG. 3.

The operation of the apparatus to provide the waveform of FIG. 6 is shown in FIG. 7. From the start 1000 a region of interest 1002 is determined. The waveform generator 900 generates an acoustic line with high acoustic amplitude (1004 and this is then followed by a time delay of preferably between 1–10 μsec 1006).

An acoustic line with low acoustic amplitude is then generated 1008 by generator 900 and the signal received at receiver 906 is analysed from the region of interest (ROI) to determine the optimal frequency 1010. The signal is interrogated to determine if generated small bubbles are present 1012. If they are then the generator generates a further line 1008. This further line is generated following a determination of optimal frequency 1014 and the line is generated after a second time delay 1016. This process is repetitive. If no generated gas bubbles are present then the output is analysed to determine how long the bubbles persisted and their initial size 1018.

It is also possible to terminate the procedure on detection of a lower limit, e.g. −55 dB (see FIG. 8) and for the time of termination to be interpolated to determine pressure, temperature or other characteristics of a medium.

What is claimed is:

1. An ultrasound contrast acoustic field generating method characterised in that said method comprises generating a first, relatively high power, acoustic field (A) for a first predetermined number of cycles, and following a predetermined time delay ($\Delta_t$) generating a second relatively lower power acoustic field (B) for a second predetermined number of cycles, said first predetermined acoustic field (A) causing, in use, power enhanced scattering of microcapsules and said second predetermined acoustic field (B) being below the threshold for power enhanced scattering and causing scattering providing information about possible generated free gas bubbles.

2. An ultrasound contrast imaging method as claimed in claim 1 in which the acoustic field has a frequency of 100 kHz to 10 MHz.

3. Apparatus for ultrasound contrast acoustic field generating characterised in that said apparatus comprises means (900) for generating a first relatively high power acoustic field for a first predetermined time period timing means (910) for generating a predetermined delay time, and means (900) for generating a second relatively low power acoustic field for a second predetermined period following said predetermined delay time.

4. Apparatus for ultrasound contrast imaging as claimed in claim 3 comprising receiver means (906) for receiving a signal in a period following the generation of the second relatively low power acoustic field.

5. Apparatus for ultrasound contrast imaging as claimed in claim 4 including the means for generating a second relatively low power acoustic field comprises further timing delay means for repeating said low power acoustic field after a further predetermined delay.

6. Apparatus for ultrasound contrast imaging as claimed in claim 5 in which the apparatus includes signal receiver means for interrogating a received signal during said further predetermined delay.

7. Apparatus for ultrasound contrast imaging as claimed in claim 6 in which the apparatus comprises time sequencing means for repetitively supplying a series of relatively low power acoustic fields with a predetermined time delay interposed between each relatively low power acoustic field and including receiver means for receiving and interrogating a received signal during each predetermined time delay.

8. Apparatus for ultrasound contrast imaging as claimed in claim 5 in which the apparatus includes means for determining from the received signal whether any generated small bubbles are still present and means for terminating said sequence of relatively low acoustic power signals on determination that no small bubbles are present.

9. Apparatus for ultrasound contrast imaging as claimed in claim 5 in which the apparatus includes means for determining from the received signal whether any generated small bubbles are still present and means for terminating said sequence of relatively low acoustic power signals on determination that only a lower limit of bubbles is present, the time period since commencement of the lower acoustic power signals providing an indication of pressure, temperature or other characteristic of the medium in which the small bubbles are present.

10. Apparatus for ultrasound contrast imaging as claimed in claim 8, said apparatus including means for selectively adjusting the insonifying frequency of the acoustic field to thereby adjust the disappearance period of the generated frequency bubbles.

11. A ultrasound method for determining a characteristic of a body, the method comprising:
   (a) generating a first acoustic field at a first power;
   (b) releasing free gas bubbles from microspheres in response to (a);
   (c) generating a second acoustic field at a second power less than the first power at a predetermined time after (a); and
   (d) determining the characteristic as a function of a response of the free gas bubbles to the second acoustic field.

12. The method of claim 11 wherein (d) comprises determining a pressure.

13. The method of claim 11 wherein (d) comprises determining a temperature.

14. The method of claim 11 further comprising (e) repeating (c) wherein (d) comprises determining the characteristic as a function of time and (e).

15. The method of claim 11 wherein (d) comprises determining the characteristic as a function of the predetermined time.

\* \* \* \* \*

UNITED STATES PATENT AND TRADEMARK OFFICE
CERTIFICATE OF CORRECTION

PATENT NO.    : 6,322,512 B1
DATED         : November 27, 2001
INVENTOR(S)   : Nico De Jong et al.

It is certified that error appears in the above-identified patent and that said Letters Patent is hereby corrected as shown below:

Column 2,
Line 31, delete "At of" and substitute -- Δt of --.
Line 36, delete "At set" and substitute -- Δt set -- .

Column 3,
Line 65, delete "oily" and substitute -- only --.

Signed and Sealed this

Fourth Day of March, 2003

JAMES E. ROGAN
*Director of the United States Patent and Trademark Office*